(12) United States Patent
Harry-O'kuru

(10) Patent No.: US 7,351,403 B2
(45) Date of Patent: *Apr. 1, 2008

(54) SUNSCREEN REAGENTS FROM UNSATURATED WAXES AND TRIGLYCERIDES

(75) Inventor: Rogers E. Harry-O'kuru, Peoria, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 809 days.

This patent is subject to a terminal disclaimer.

(21) Appl. No.: 10/463,491

(22) Filed: Jun. 17, 2003

(65) Prior Publication Data

US 2004/0258635 A1 Dec. 23, 2004

(51) Int. Cl.
A61Q 17/04 (2006.01)
A61Q 19/04 (2006.01)
A61Q 19/00 (2006.01)
A61K 8/02 (2006.01)

(52) U.S. Cl. .......... 424/59; 424/60; 424/400; 424/401

(58) Field of Classification Search .......... 424/59, 424/60, 400, 401
See application file for complete search history.

(56) References Cited

U.S. PATENT DOCUMENTS

| | | |
|---|---|---|
| 5,676,994 A | 10/1997 | Eskins et al. |
| 5,882,713 A | 3/1999 | Eskins et al. |
| 5,989,528 A | 11/1999 | Tanner et al. |
| 6,346,236 B1 | 2/2002 | Compton et al. |
| 2004/0258743 A1* | 12/2004 | Compton et al. ........... 424/450 |

FOREIGN PATENT DOCUMENTS

WO   WO 02/079121   10/2002

OTHER PUBLICATIONS

Knudsen et al., "The Milkweed Business", http://www.hort.purdue.edu/newcrop/proceedings1993/v2-422.html, 1993, p. 422-428, In: J. Janick and J. E. Simon (eds.), New Crops. Wiley, New York.

McGraw, Linda, "New Uses for Milkweed", http://www.ars.usda.gov/is/r/1999/991001.html, Oct. 1, 1999.

* cited by examiner

*Primary Examiner*—Shelley A. Dodson
(74) *Attorney, Agent, or Firm*—John D. Fado; Randall E. Deck; Lesley Shaw

(57) ABSTRACT

A class of UVA- and UVB-absorbing esters has been derived from milkweed oil by modification with a variety of cinnamic acids. These agents have the advantage of being synthesized from natural materials, while providing a value-added use for the oil. They are readily formulated into standard UV-absorbing daily-wear cosmetic, hair and skin care, and sunscreen formulations.

11 Claims, No Drawings

SUNSCREEN REAGENTS FROM UNSATURATED WAXES AND TRIGLYCERIDES

CROSS REFERENCE TO RELATED APPLICATION

This application is related to commonly assigned application Ser. No. 10/462,882, filed concurrently herewith, by David L. Compton, Terry A. Isbell and Rogers E. Harry-O'kuru, entitled "Novel Sunscreen Reagents from Hydroxy-Substituted Acylglycerides", herein incorporated by reference in its entirety.

BACKGROUND OF THE INVENTION

1. Field of the Invention

This invention relates to methods for modifying milkweed oil with cinnamic acids to form ultraviolet (UV)-A and (UV)-B absorbing esters.

2. Description of the Prior Art

Health hazards associated with exposure to the sun are well established. The short term effect of excessive exposure to sunlight is erythema, commonly referred to as sunburn. Sunburn is primarily the result of UVB radiation having a wavelength of from about 290 nm to about 320 nm. Long term effects of exposure to sunlight include skin cancer (melanoma) and premature aging of the skin (including wrinkling, loss of elasticity, and pigment changes). These effects are predominantly caused by UVA radiation having a wavelength of from about 320 nm to about 400 nm. Public awareness of the dangers of sun exposure has stimulated the market for personal care products containing sunscreens.

Sunscreens function either as ultraviolet (UV) filters or UV blocks. UV blocks, such as $TiO_2$ and ZnO, as well as derivatives of other metal-oxides, form a physical barrier that scatters UV light (Fairhurst et al., "Particulate Sun Blocks: General Principles", Sunscreens: Development, Evaluation, and Regulatory Aspects, 2nd Edn, pp. 313-352, 1997). These UV blocks offer the most comprehensive sunscreen protection, blocking the full spectrum of UVA (400-320 nm) and UVB (320-290 nm) light. As a result of the particulate nature of these formulations, they often leave a noticeable residue when applied to the skin, which is cosmetically unacceptable to the consumer. The most commonly used sunscreens are UV filters, which are typically organic compounds incorporated at levels of about 2-15% into topical formulations (N. A. Shaath, "Evolution of Modern Sunscreen Chemicals", Ibid, pp. 3-33, 1997), (N. A. Shaath, "Quality Control of Sunscreens", Ibid, pp. 657-676, 1997). A disadvantage of UV filters is that each organic compound has a limited range of maximum UV absorptivity, rendering each reagent better suited for either UVA protection or UVB protection but not both. The advantage of the UV filtering molecules, however, is that they can be engineered to provide sunscreens with desirable physical appearance, solubility, and water resistant properties (N. A. Shaath, "Quality Control of Sunscreens", Ibid, pp. 657-676, 1997).

Although no longer used today, benzyl cinnamate formulated as an emulsion with benzyl salicylate, was used as a sunscreen as early as 1928 (N. A. Shaath, "Evolution of Modern Sunscreen Chemicals", Ibid, pp. 3-33, 1997). Today, cinnamic acid derivatives are the most widely used UVB absorbing chemicals in sunscreen formulations, with four derivatives approved for use in the United States and 17 approved for use in Europe (N. A. Shaath, "Evolution of Modern Sunscreen Chemicals", Ibid, pp. 3-33, 1997). The unsaturated C=C bond adjacent to the aromatic ring in cinnamates allows for a continuous, conjugated p-system throughout the molecule. An electron can be delocalized throughout the p-system by photo-excitation with energy corresponding to about 305 nm. Most common cinnamic acids and short chain esters are water soluble, limiting their usefulness as waterproof sunscreens. Cinnamic acid derivatives, therefore, have been designed with long chain hydrocarbons (i.e. octyl-p-methoxy cinnamate), which renders them water-insoluble and suitable for waterproof sunscreens. The —$OCH_3$ group of octyl-p-methoxy cinnamate acts as an electron-releasing group to improve the electron excitation process (N. A. Shaath, "Evolution of Modern Sunscreen Chemicals", Ibid, pp. 3-33, 1997).

There is currently a growing interest in modifying fats and oils to form structured lipids with specific properties for nutritional and pharmaceutical applications. Recent reviews have outlined the strategies for synthesizing tailor-made fats and oils and their desired properties (Willis et al., "Lipid Modification Strategies in the Production of Nutritionally Functional Fats and Oils", Crit. Rev. Food Sci. Nutr. 38:639-674, 1998), (F. D. Gunstone, "Movements Towards Tailor-Made Fats", Prog. Lipid. Res. 37:277-305, 1998). These strategies have included blending, distillation, fractionation, hydrogenation, interesterification with chemical catalysts, and more recently interesterification with biocatalysts. Chemical interesterifications of triacylglycerols for industrial applications are typically performed using inorganic catalysts at elevated temperatures (200-250° C.) (N. N. Gandhi, "Applications of Lipase", J. Am. Oil Chem. Soc. 74:621-633, 1997). Enzymatic interesterifications, however, offer the advantages of milder reaction conditions, a wider variety of synthetic substrates, and regioselective specificity towards the acyl groups of the triglycerols (Schmid et al., "Lipases: Interfacial Enzymes with attractive Applications", Angew. Chem. Int. Ed. 37:1608-1633, 1998).

Compton et al. (U.S. Pat. No. 6,346,236 hereby incorporated by reference) teaches the formation of sunscreens from vegetable oil and plant phenols by use of a lipase catalyzed transesterification reaction to yield novel ferulyl-substituted or coumaryl-substituted acylglycerols.

Apart from the aforementioned efforts to develop improved sunscreen agents, there has been a resurgence in recent years to cultivate the common milkweed (Asclepias syriaca L.) as an alternative crop (Knudsen, H. D. et al., 1993, the Milkweed Business, pp. 42-428, In: J. Janick and J. E. Simon (eds), New Crops, Wiley, N.Y.), with the primary focus on marketing the floss as a substitute for waterfowl down. A byproduct of floss production is the seed which is rich in milkweed oil composed of 45-50% linoleic acid.

SUMMARY OF THE INVENTION

We have now invented a novel class of UVA- and UVB-absorbing esters derived from milkweed oil modified by reaction with a variety of cinnamic acids. These agents have the advantage of being synthesized from natural materials, while providing a value-added use for the oil. They are readily formulated into standard UV-absorbing daily-wear cosmetic, hair and skin care, and sunscreen formulations.

In accordance with this discovery, it is an object of this invention to provide feruloyl-, coumaroyl-, sinapoyl- or o-methylsinapoyl-substituted milkweed oil, having utility as sunscreen and antioxidants agents.

It is also an object of the invention to produce a sunscreen agent that provides broad spectrum UV (both UVA and UVB) protection.

Another object of the invention is to incorporate the feruloyl, coumaroyl, sinapoyl- or o-methylsinapoyl-substituted acylglycerols of the invention into daily-wear cosmetic, hair and skin care, and sunscreen formulations.

A further object of the invention is to produce sunscreen agents that have the advantage of being synthesized from natural materials, while providing value-added use for vegetable oils.

Another object of the invention is to convert milkweed oil to the aforementioned cinnamic acid derivatives by relatively simple and inexpensive processes via epoxy and hydroxy intermediates.

Other objects and advantages of this invention will become readily apparent from the ensuing description.

DETAILED DESCRIPTION

The milkweed oil starting material for use herein may be any milkweed seedmeal pressing or refined fraction thereof. Though the current primary source of milkweed oil is seed from the common milkweed (*Asclepias syriaca* L.), oil from other species of milkweed having a similar fatty acid profile (high in linoleic acid) could also be used.

The sunscreen compounds of the invention are produced by derivatizing the milkweed oil with a cinnamic acid selected from the group of ferulic, coumaric, sinapic, and o-methylsinapic acids to form esters at or near the sites of unsaturation. These acids are illustrated by Formula I, below.

Structures of Various Cinnamic Acids

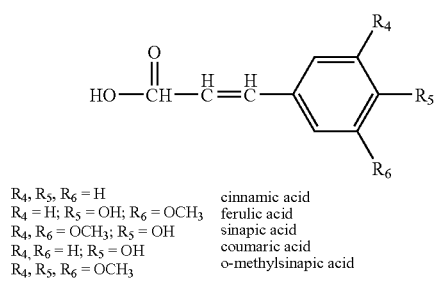

Formula I $R_4, R_5, R_6 = H$     cinnamic acid
$R_4 = H; R_5 = OH; R_6 = OCH_3$     ferulic acid
$R_4, R_6 = OCH_3; R_5 = OH$     sinapic acid
$R_4, R_6 = H; R_5 = OH$     coumaric acid
$R_4, R_5, R_6 = OCH_3$     o-methylsinapic acid Esterification is conducted through an epoxy intermediate formed by epoxidizing one or more of the olefinic groups (sites of unsaturation) present in the acyl substituents (fatty acid side chains) of the milkweed triglyceride. The milkweed oil fatty acid profile as reported by Natural Fibers Corporation (www.buymilkweed.com/oil profile.htm) is reproduced in Table I, below. A total of 42% of the fatty acids are monounsaturated, 47% are diunsaturated (predominantly linoleic acid), and the level of triunsaturated fatty acids (linolenic) is minimal. This fatty acid profile offers a platform for unique distribution of the cinnamic acid functionality. In a preferred embodiment of the invention, all, or nearly all, the available sites of unsaturation are derivatized with two cinnamate moieties per original site of unsaturation. However, if desired, the stoichiometry of the reactants or conditions of reaction (as described below), may be selected for achieving only partial derivatization.

Epoxidation may be carried out as described by Qureshi et al. [*Polymer Science and Technology*, Vol. 17, Plenum Press, p. 250] or by any other method as known in the art. For example, the epoxidation may be carried out by reaction of the milkweed oil with formic acid and hydrogen peroxide at an elevated temperature on the order of 75° C. The degree of epoxidation should be such that there is at least 2, and preferably at 3, or even 4, oxirane rings per triglyceride molecule. Typically, the epoxidation is carried to completion.

Conversion of the oxirane rings of the epoxidized oil to hydroxy substituents is readily conducted in the presence of a strong acid, such as HCl, $HNO_3$, $H_2SO_4$, etc. at a temperature ranging from about 50° C. to about 200° C.

Esterification of hydroxy or epoxy fatty acid moieties with the cinnamic acid is optimally conducted in the absence of oxygen at a temperature ranging from about 150° C. to about 250° C. for a period of time ranging from about 12 to 72 hours. Alternatively, esterification of hydroxy or epoxy fatty acid moieties may be carried out with the use of acid catalyst such as $ZnCl_2$, p-toluenesulfonic acid, tin(II) 2-ethylhexanoate, tin octanoate, tin chloride and $BF_3$ in toluene, tetrahydroxyfuran, dimethylformamide or another suitable solvent for the reactants at a temperature in the range of about 80° C. to about 150° C. for a period of time ranging from about 1 to 3 hours.

Scheme 1, illustrated below, shows the esterification of milkweed oil with ferulic acid via the epoxide and hydroxyl derivatives to produce the ferulyl-milkweed oil ester. Formic acid in the presence of peroxide is reacted with the unsaturated triglyceride at a temperature on the order of 75° C. The epoxide may then be directly esterified with ferulic acid in the presence of $ZnCl_2$ at 110° C. Alternatively, each oxirane ring is opened by means of a strong acid catalyst to yield a dihydroxy intermediate, and then reacted with ferulic acid using $ZnCl_2$ or other acid catalyst (as described above) to yield the ferulated milkweed ester.

Scheme 1

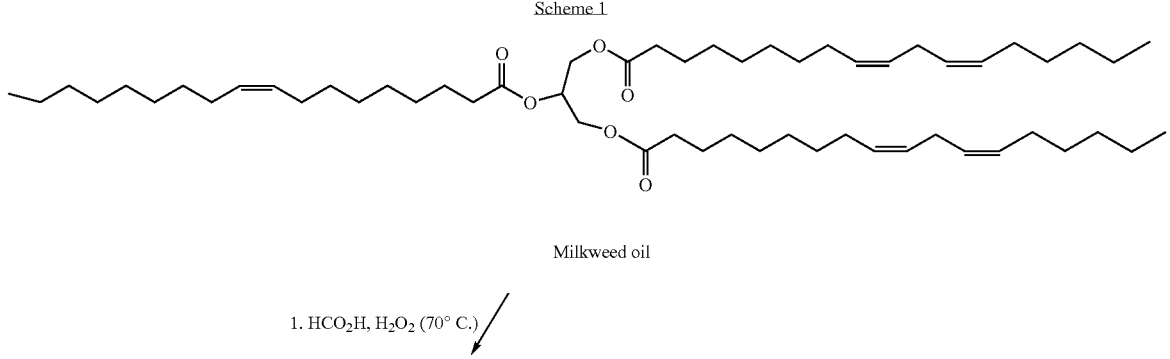

Milkweed oil

1. $HCO_2H$, $H_2O_2$ (70° C.)

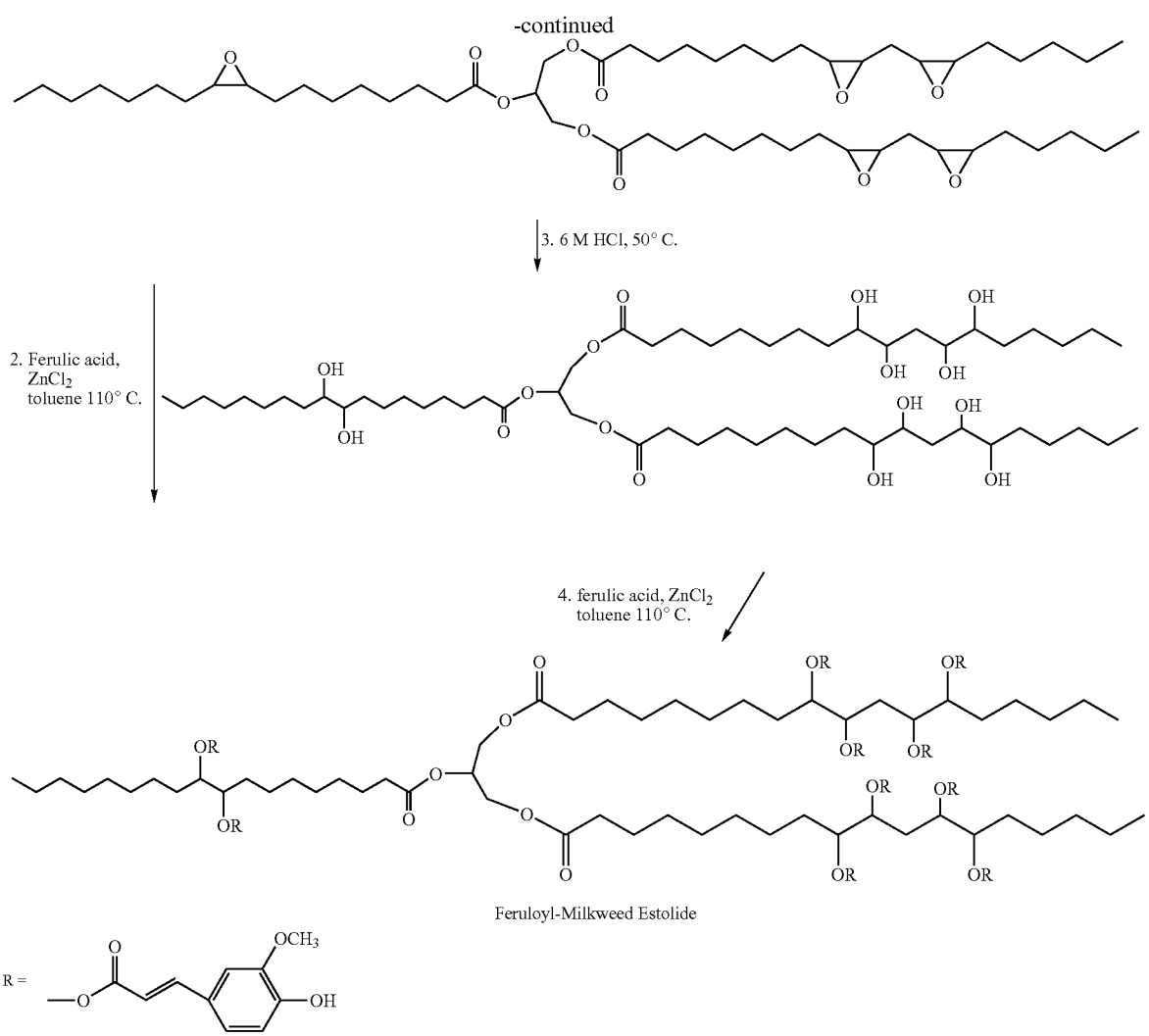

Feruloyl-Milkweed Estolide

The milkweed oil cinnamate esters of this invention, having at least 4, preferably at least 6, and more preferably at least 8 cinnamate moieties per triglyceride molecule, are characterized by the water-insoluble properties of a lipid that resists being washed off in water. The UV absorbance of these products extends from about 280 nm to about 350 nm, and they are particularly effective in absorbing UV in the range of about 310 to about 350 nm. This is predominantly in the UVA range, but also covers part of the UVB range. For additional UVB protection, the subject compounds may be formulated with other sunscreen agents as discussed, below.

The sunscreen agents of the invention may be formulated into any cosmetic preparations that are especially designed to be water-resistant. The total level of sunscreen agent in these preparations will typically be on the order of about 0.1 to 20%, by weight, and preferably within the range of about 1 to about 15%, by weight. The amount of sunscreen agent currently approved in the United States for inclusion in a topical skin treatment formulation is 15% by weight. It is contemplated that the agents of this invention will be incorporated into formulations that are both effective and safe. An effective amount (or photoprotective amount) is that amount which is sufficient to significantly induce a positive effect of protection against UV sunlight as compared to a control. One measure of the effectiveness of the sunscreen agent is the Sun Protection Factor (SPF) of the composition. SPF is a commonly-used measure of photoprotection of a sunscreen against sunburn. The SPF is defined as the ratio of the UV energy required to produce minimal erythema on protected skin to that required to produce the same minimal erythema on unprotected skin in the same individual (See Federal Register, 43, No. 166, pp. 38206-38269, Aug. 25, 1978). A safe amount is that which does not produce serious side effects.

The cosmetic preparations according to the invention can be formulated as a lotion, cream, gel, stick or aerosol. The base of the formulation may be a water-in-oil emulsion, an oil-in-water emulsion, an oil-in-oil alcohol lotion, a vesicular dispersion, or as an emulsifier-free starch/lipid dispersions as described in U.S. Pat. Nos. 5,676,994 and 5,882,713, both herein incorporated by reference. The term "oil" is used herein to be inclusive of all lipids. The term "lipid" (or fat) is a comprehensive term referring to substances which are found in living cells and which are comprised of only a non polar hydrocarbon moiety or a hydrocarbon moiety with polar functional groups (see the Encyclopedia of Chemistry, 3rd Edition, C. A. Hampel and G. G. Hawley, eds., 1973, p. 632, herein incorporated by reference). Most lipids are insoluble in water and are soluble in fat solvents such as ether and chloroform. Commonly used oils for cosmetic formulations include coconut oil, silicone oil and jojoba oil.

Other components that may be included in the sunscreen formulations of the invention include: other UVA and UVB sunscreen agents, such as 2-phenyl-benzimidazole-5-sulfonic acid, TEA salicylate, octyl dimethyl PABA, padimate-O (2-ethylhexyl 4-(dimethylamino) benzoate) and octyl methyl cinnamate; inorganic physical sunblocks, such as zinc oxide and $TiO_2$; artificial tanning agents; abrasives; absorbents; fragrances; pigments; colorings/colorants; essential oils; skin sensates; astringents carriers and vehicles; thickening/structuring agents; emollients; emulsion stabilizers; excipients and auxiliaries commonly incorporated into cosmetic formulations; humectants; moisturizers; skin conditioners; anti-caking agents; antifoaming agents; antimicrobial agents; antioxidants; binders; buffering agents; bulking agents; chelating agents; chemical additives; film formers; humectants; opacifying agents; skin-conditioning agents; vitamins; and the like. Suitable emulsifiers include any of those conventionally used for cosmetic formulations, including for example, ethoxylated esters of natural derivatives, such as polyethoxylated esters of hydrogenated castor oil, a silicone oil emulsifier such as silicone polyol, free or ethoxylated fatty acid soap, an ethoxylated fatty alcohol, a free or ethoxylated sorbitan ester, an ethoxylated fatty acid or an ethoxylated glyceride. Exemplary agents and additives that could be included in formulations comprising the sunscreen agents of the invention, as well as suggested levels of addition, are given in U.S. Pat. No. 5,989,528 (Tanner et al.), which is herein incorporated by reference.

As previously indicated, the compositions of the invention are useful as sunscreen agents to provide protection from adverse effects of UV radiation. The principal application is as a topical sunburn protectant for human skin. However, it is envisioned that the compositions and formulations of the invention would also have veterinary applications as a skin protectant. The sunscreen formulations contemplated herein may be applied to the skin by spreading or spraying a thin layer thereof over the skin surface intended to be protected.

It is envisioned that the compounds of this invention may also have certain industrial applications, such as a UV protectant for epoxies, paints, and other consumer products. For these applications, the compounds could either be formulated into the material to be protected, such as by blending into a paint, or they could be applied as a separate coating.

The following example is intended to further illustrate the invention, without any intent for the invention to be limited to the specific embodiments described therein.

EXAMPLE 1

Synthesis of Feruloyl-Milkweed Ester Using a Catalyst

Synthesis of Polyepoxymilkweed Oil from Milkweed Oil.

In a typical process, refined milkweed oil 582.0 g (673.76 mmol, iodine value, IV=111.4) was placed in a 1 L 3-necked jacketed flask equipped with a mechanical stirrer and heated to 45.5° C. Formic acid (96%, 39.7 g, 0.3 equiv./mol of C=C) was added and the mixture stirred to homogeneity. Hydrogen peroxide (50%, 320 mL, 6.74 mol) was added slowly (i.e. drop wise). At the end of hydrogen peroxide addition, the temperature was raised to 70° C. and vigorous stirring was continued for 7 hours. The heat source was then removed, the reaction mixture allowed to cool and transferred to a separatory funnel with ethyl acetate as diluent. The material was washed with saturated NaCl (300 mL×4) followed by saturated $Na_2CO_3$ (35 mL) in more NaCl solution. When pH 7.5 was reached, the organic phase was then washed with deionized water. The wet organic layer was separated from a turbid aqueous phase and was concentrated at 60° C. in vacuo to remove the solvent and water. Yield of epoxy triglyceride was 558.4 g; the kinematic viscosities, measured were: $\eta_{40°\ C.}$=1208.95 cs and $\eta_{100°\ C.}$=81.3 cs, that is, a viscosity index of 18.79 cs/° C. PV=9.4, IV=1.79. Specific rotation $[\alpha]_D^{20}$=+0.17° (0.065, $CH_2Cl_2$). An aqueous fraction (42.0 g) was reclaimed from the final water-wash following concentration at 70° C., thus giving a total yield of 600.6 g (97%).

Synthesis of Polyhydroxymilkweed Oil from Milkweed Oil.

In a 1 L jacketed flask as described above, reprocessed milkweed oil (648.0 g, 759.9 mmol) was introduced. The oil was stirred vigorously at 40° C. and formic acid (90.4%, 62.2 g, 1.22 mol) was added in one portion followed with a slow (drop wise) addition of $H_2O_2$ (50%, 203.0 g, 2.98 mol). At the end of peroxide addition, the temperature was increased to 70° C. After 15 h, the heat source was removed but stirring was continued, allowing the reaction mixture to cool to room temperature and the aqueous phase removed. Deionized water (300 ml) was added followed by 6 M HCl (100 ml). The nearly colorless sludge was stirred at 70° C. overnight. The cream colored product was transferred into a separatory funnel using ethyl acetate as diluent. The aqueous layer was discarded and the organic phase washed sequentially with brine, saturated $NaHCO_3$ to pH 7.5, and deionized water. Ethanol was added to facilitate separation of the phases. After removal of the aqueous layer, the product was concentrated in vacuo at 70° C. to yield 711.6 g (94.7%) of the polyhydroxyl triglyceride with an oxirane value=1.35; iodine value=14 compared to an iodine value of 114 in the starting milkweed oil. The measured kinematic viscosities were: $\eta_{40°\ C.}$=2332.5 centistokes and $\eta_{100°\ C.}$=75.53 centistokes, that is, a viscosity index of 37.62 centistokes/° C. Specific rotation $[\alpha]_D^{20}$=+0.37°.

Synthesis of Feruloyl-milkweed Ester from Polyhydroxymilkweed Oil.

Milkweed polyhydroxytriglyceride 34.40 g (38.5 mmol), glacial acetic acid (150 ml), 4-hydroxy-3-methoxycinnamic acid (ferulic acid, 45.0 g, 231.7 mmol), HCl (12.1 M, 4.5 ml), ethyl acetate (250 mL) were placed in a 1 L three-necked round bottomed flask equipped with a mechanical stirrer. The contents of the reaction flask were stirred and heated to gentle reflux. Progress of the reaction was monitored by TLC (hexanes/ethyl acetate: 1:1 v/v) on precoated silica gel. After 36 h, the reaction mixture was allowed to cool to room temperature, diluted with more ethyl acetate and transferred into a separatory funnel. The solution was washed with deionized water (300 mL×4) to remove most of the acetic acid. The organic phase was then washed with saturated disodium monohydrogen phosphate solution and deionized water until the washings were about pH 7. The reddish tinged organic solution was dried ($Na_2SO_4$) and concentrated in vacuo to give a crude product, 64.0 g (81%). The crude product was purified by volume liquid chromatographic (VLC) technique on silica gel with hexanes/ethyl acetate (1:1) as the eluting solvent. The desired fraction yield was 44.50 g (56.5%) based on the hexaferuloyl ester.

All references disclosed herein or relied upon in whole or in part in the description of the invention are incorporated by reference.

TABLE I

Milkweed Oil Fatty Acid Profile

| Carbon Chain | Component Name | % of Total Fatty Acid |
|---|---|---|
| C16:0 | Palmitic | 5.83 |
| C16:1 | Palmitoleic | 6.99 |
| C17:0 | Margaric | 0.10 |
| C17:1 | Margaroleic | 0.13 |
| C18:0 | Stearic | 2.41 |
| C18:1 | N-7 Cis (delta 11) Vaccinic | 14.36 |
| C18:1 | N-9 Cis (delta 9) Oleic | 20.87 |
| C18:2 | Linoleic | 47.16 |
| C18:3 | Linolenic | 1.24 |
| C20:0 | Arachidic | 0.33 |
| C20:2 | Eicosadienoic | 0.20 |
| C22:0 | Behenic | 0.11 |
| C22:1 | Erucic | 0.10 |
| C24:0 | Lignoceric | 0.15 |
|  | TOTAL | 100% |

I claim:

1. A modified triglyceride milkweed oil comprising C16-C18 acylmoieties substituted with one or more cinnamate moieties selected from the group consisting of cinnamoyl, feruloyl, coumoroyl, sinapoyl, and o-methylsinapoyl.

2. The milkweed oil of claim 1 wherein at least one of said cinnamate moieties is cinnamoyl.

3. The milkweed oil of claim 1 wherein at least one of said cinnamate moieties is feruloyl.

4. The milkweed oil of claim 1 wherein at least one of said cinnamate moieties is o-methylsinapoyl.

5. The milkweed oil of claim 1 wherein the average number of cinnamate moieties per molecule of said oil is at least 4.

6. The milkweed oil of claim 1 wherein the average number of cinnamate moieties per molecule of said oil is at least 6.

7. The milkweed oil of claim 1 wherein the average number of cinnamate moieties per molecule of said oil is at least 8.

8. A method of making a modified triglyceride milkweed oil comprising C16-C18 acyl moieties substituted with one or more cinnamate moieties selected from the group consisting of cinnamoyl, feruloyl, coumoroyl, sinapoyl, and o-methylsinapoyl comprising the steps:

a) epoxidizing said triglyceride milkweed oil at one or more sites of unsaturation on C16-C18 acyl moieties in said oil to produce an epoxidized triglyceride milkweed oil having one or more sites of epoxidation;

b) modifying said one or more sites of epoxidation by esterification with an acid selected from the group consisting of cinnamic acid, ferulic acid, coumaric acid, sinapic acid, and 0-methylsinapic.

9. The method of claim 8, wherein said esterification comprises converting said epoxidized triglyceride milkweed oil to a synthetic hydroxy-containing acylglyceride intermediate by hydroxylating said one or more sites of unsaturation to produce one or more hydroxylated sites and reacting said hydroxylated sites with said acid.

10. The method of claim 8, wherein said esterification comprises reacting said one or more sites of epoxidation with said acid in the presence of a catalyst.

11. The method of claim 10, wherein said catalyst is a strong acid.

* * * * *